United States Patent [19]

Eberwine et al.

[11] Patent Number: 5,723,290

[45] Date of Patent: Mar. 3, 1998

[54] METHODS FOR PROFILING MRNA EXPRESSION IN NEURITES

[75] Inventors: James Eberwine, Philadelphia; Marc Dichter, Penn Valley; Kevin Miyashiro, Philadelphia, all of Pa.

[73] Assignee: Trustees of the University of Pennsylvania, Philadelphia, Pa.

[21] Appl. No.: 334,254

[22] Filed: Nov. 3, 1994

[51] Int. Cl.$^6$ .............................. C12Q 1/68; C07H 21/04; C12P 19/34

[52] U.S. Cl. ................... 435/6; 435/91.2; 435/91.21; 435/91.51; 536/23.5; 536/24.31; 935/17; 935/18; 935/77; 935/78

[58] Field of Search .................... 435/6, 91.2, 91.21, 435/91.51; 536/23.5, 24.31; 935/17, 18, 78, 77

[56] References Cited

PUBLICATIONS

Craig et al., "The Distribution of Glutamate Receptors in Cultured Rat Hippocampal Neurons: Postsynaptic Clustering of AMPA–Selective Subunits," *Neuron* 1993, 10, 1055, 1068.

Chicurel et al., "mRNA at the Synapse: Analysis of a Synaptosomal Preparation Enriched in Hippocampal Dendritic Spines," *J. Neurosci* 1993, 13, 4054–4063.

Liang et al., "Differential Display of Eukaryotic Messenger RNA by Means of the Polymerase Chain Reaction," *Science* 1993, 257, 967–971.

Gennaro, A., Ed., *Remington's Pharmaceutical Sciences*, 18th Ed., 1990.

Eberwine et al, Proceedings National Academy of Sciences, USA (1992) 89: 3010–3014.

*Primary Examiner*—Carla J. Myers
*Attorney, Agent, or Firm*—Law Offices of Jane Massey Licata

[57] ABSTRACT

A method of identifying neurite cDNA clones by determining and comparing mRNA expression in selected neurites is provided. cDNA clones identified by this method are also provided. In addition, methods of profiling mRNA expression and diagnosing and treating conditions associated with a pattern of mRNA expression by determining an mRNA expression profile are provided.

5 Claims, 3 Drawing Sheets

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 200
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 1:

```
CCTGGNACNC  AAGCATCTTN  CACCGAACCN  TCCNAAAGTN  CTGGAATTAN   50

AGTATTNAAG  TACATCTAAG  TAATGNACTG  TAAANTNAAA  ATTAANTTAA  100

ANTTTCANTN  ATTATNAANA  TGAGCTTCGT  GCATGTAATA  TTGTCGNAAC  150

AAAAGGTGCT  TNATGGNANC  CTTCTAANGT  ATAGTCTCTA  AAGNCCTGTT  200
```

( 2 ) INFORMATION FOR SEQ ID NO: 2:

( i ) SEQUENCE CHARACTERISTICS:
        ( A ) LENGTH: 434
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 2:

```
AGGGGTCTTG  CCAACANTNN  AATTCCTTCG  GNAGAATGTA  AGCNCCATAA   50

GGGCAGGGGC  CACATCTACC  CACTNACCTN  ATGTCCCCAG  CGCTTAGCCT  100
```

```
AGTGTNTGGA  ACATTNAAGG  TGCTCAACCC  TTTTNTAGAA  TNAATAAATN   150

AATGAAGGCA  CACAACGTGC  CGAANATTTA  AANGTATTGG  AGATCTTNTN   200

TTTAANATGG  NNAAATAGAG  AGCCCAGTAT  TATTTAAAAT  GTCAGCAATG   250

GGCAAGGCTT  CAACCCCAG   TCTTCTGGCT  TTTGCCATCC  AATACATCCC   300

NCTACTTCCC  ATCTANAATN  ATGCCTTCCT  TTGTNTAGTN  ATCTTGCTTT   350

ACCTTTGCNA  TTTACCTCGC  TCAAGTTCAA  CTTTTCAGTN  GCAAGCCTTG   400

GCCCNCAAGN  CCTGCCGCGG  NTCAAAGCCC  CCTG                     434
```

( 2 ) INFORMATION FOR SEQ ID NO: 3:

( i ) SEQUENCE CHARACTERISTICS:
        ( A ) LENGTH: 404
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 3:

```
GGGTAGAAAT  GTCANTTCCC  ATGAAGGGCA  GGGGCCACAT  CTACCCACTC   50

ACCTNATGTC  CCCAGCGCTT  AGCCTAGTGT  CTGGNACATT  GAAGGTGCTC   100

AACCCTTTTG  TAGAATGAAT  AAATGAATGA  NGGCACACAA  CGTGCCGAAC   150

ATTTNAANAT  ATTGGAGATC  TTGTTTTTAA  NATGGGAAAA  TAGAGAGCCC   200

AGTATTATTT  AAAATGTCAG  CAATGGGCAA  GGCTTCAACC  CCCAGTNTTC   250

TGGCTTTTGC  CATCCAATAC  ATCCCACTAC  TTCCCATCTA  AAATNATGCC   300

TTCCTTTGTA  AAGTNATCTT  GCTTTTACCT  TTGCNATTAC  CTCGCTCAAG   350

TTCACTTTTC  AGTAGCAAGC  CTGGGCCCAC  AAGGCCTGCC  NCGGTCAANA   400

CCCT                                                         404
```

( 2 ) INFORMATION FOR SEQ ID NO: 4:

( i ) SEQUENCE CHARACTERISTICS:
        ( A ) LENGTH: 261
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 4:

```
AGGGGTCTTG  GAACAAGAAA  TGNNNNTNNN  NNNNNATCTG  CAGGCTGGAA   50

GTCCCAGAGC  ACAGTGTCTG  CAGGGTNGGN  TTCTCCCAAG  GCCTCTNTCC   100

TTGCNTTGTA  GACGGCCACC  TGTNCTCTGT  GTCCTCTNAC  AGTNNTCCNT   150

CTGTNTNTNT  CTNNNTAATA  ATCTCCCCTT  CATAAAAGGA  CACCAGTCAC   200

TCTGGATTAG  GGCTCACTCT  AGTAGCCTNN  TCTAACATCC  NTNACCTCTT   250

TNAAGACCCC  T                                                261
```

( 2 ) INFORMATION FOR SEQ ID NO: 5:

( i ) SEQUENCE CHARACTERISTICS:
        ( A ) LENGTH: 141
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 5:

| | | | | |
|---|---|---|---|---|
| AGGGGTCTTN | CAGAGGAACA | AAGGAATCNC | NCTACAGGNC | TCTTTNCTNA 50 |
| NTNANGGACA | ACNNNAAACA | AGTCCTTTAN | GCAGGCTAAG | GTCTACATGC 100 |
| NTCTNTCCAT | GCAAATCCNG | AATATGGCTC | CCAAGACCCC | T           141 |

( 2 ) INFORMATION FOR SEQ ID NO: 6:

( i ) SEQUENCE CHARACTERISTICS:
        ( A ) LENGTH: 141
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 6:

| | | | | |
|---|---|---|---|---|
| AGGGGTCTTG | CAGAGGAACA | AAGGAATCGC | TCTACAGGTC | TCTGTACTGA 50 |
| GTGAAGGACA | ACTTCAGACA | AGTNCTTTNA | GCAGGCTAAG | GTCTACATGC 100 |
| ATCTATCCAT | GCAAATNCAG | AATATGGCTC | CCAAGACCCC | T           141 |

( 2 ) INFORMATION FOR SEQ ID NO: 7:

( i ) SEQUENCE CHARACTERISTICS:
        ( A ) LENGTH: 489
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 7:

| | | | | |
|---|---|---|---|---|
| AGGGGTCTTG | TCTTGGAGCT | GTGTTAATAC | AGCAAGCACA | GTATGTATAT 50 |
| TGCATGTNAC | AGATCAATAA | ACATGGTAAG | ACTTTCTAAA | AATNCTTTTA 100 |
| ATTCACACTT | TACTTAAGAT | TAAGAAACCT | CAAAAACACC | AAAGTGTGGT 150 |
| AGGGGTGTAG | CAGGGGAGAC | ACAAAAGAAG | AGACAGGAAG | GGGCTGAGAC 200 |
| CCTAAGCTCC | AGAAGAGGTA | TGTNATAAAA | TGAGTGGGNT | AATAAATTCC 250 |
| TTGGTGAAGT | ATGTTTTTNA | NCAACAAAAA | AATTGAAGAT | GAATGTTTAT 300 |
| CCTAGCATGG | TAAAATGTGT | GGTATGAAGG | CAGCACCCAC | TGGTTTTAAG 350 |
| AGTCTATTAG | TCTGTGAATA | TCTGNTCTCA | CTCAATTATA | ACTAAAGGAA 400 |
| TAATTTCCTA | GTNTTCAGGA | ATTTGNAAAT | TTCCNCAAAT | GTGCTTTNNG 450 |
| GNCCAAGGNT | TTTTTCAAGC | CNACNCCCNA | AGCCCCNTG  |            489 |

( 2 ) INFORMATION FOR SEQ ID NO: 8:

( i ) SEQUENCE CHARACTERISTICS:
        ( A ) LENGTH: 422
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 8:

| | | | | |
|---|---|---|---|---|
| AAAACAGGTN | AGGACNCTCN | AAAAATGCCA | NNTNAATTCA | CACTTTACTT 50 |
| AAGANTATGA | AACCNCAAAA | NCACCAAAGT | NTNGTAGGGG | TGTAGCAGGG 100 |
| GNGACACAAA | CGAAGAGNNA | GGAAGGGGCT | GNGACCCNAA | GCTCCAGAAG 150 |

```
AGGTATNTNA  TAAAATTAGT  GGGATAATAA  ATNCCNNNGT  GAAGTATGTT   200

TTTAAACAAC  AAAAAAATNG  ANGATGNATG  TTTANCCTAG  CATGNCNAAN   250

TGTGTGGTAT  GANGGCAGCA  CCCNCTGGTT  TTAAGAGCCT  ANTAGGCGTG   300

TNGATANCTG  ATCTCACTCA  NTNNTAGCNN  GNGAAGTACN  TCCTNGNNGT   350

NCNGAACTTG  TAAATTTTCN  GAAAGGTGTT  TNTGGTNACA  GGTTNTTTNA   400

AGCCAATCNC  TCAGGNCCCC  TG                                   422
```

( 2 ) INFORMATION FOR SEQ ID NO: 9:

( i ) SEQUENCE CHARACTERISTICS:
        ( A ) LENGTH: 136
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 9:

```
AGGGGTCTTG  TNAGTNAATT  GTNACTTTAA  TCATTTGGAA  ATAACCTTCT    50

TTNCTNTNAA  TATTTNAGGT  ATCTNTTTTG  TAAACAGCAT  ACACAGTAGT   100

CCCCACTTAG  CAGAGGGGGA  TAGTTCCAAG  ACCCCT                   136
```

( 2 ) INFORMATION FOR SEQ ID NO: 10:

( i ) SEQUENCE CHARACTERISTICS:
        ( A ) LENGTH: 427
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 10:

```
AGGGGTCTTG  AGATATAATT  CAGGTGCCAC  ACAATTTACC  ATTTAANGTG    50

TACAATTCAA  TGGTTTTNGG  TATATTACAT  TATTTACTTT  TNAAGCNGTG   100

GTAAAATATA  CATAACATAA  AATTNGCCAT  TTNAACATTT  TAAATGTGCA   150

ATTCAGTGGC  ATTAGTNGTA  TTCACAATGT  TATGCAACCA  TCACCAGTAT   200

TTNNNTAACT  TTTNATCACC  CCAAACAAAA  ATTCTGTAAC  CATTAAGCAG   250

TAACTNTNTN  CTCCTCTNGT  CCTGTCTTTG  ATAACTTCTA  ATCTGTTTTN   300

NGTCTCTATG  AATTNGCCCA  TTCTNCTCTG  GGGATTTACT  AGACATTTNG   350

TATGAGTGGA  ATTATCTAAN  ANTGGTNCNT  TGCTGTTTGA  CTTATTTCAC   400

CCAGTATAGN  ATGTNCAANG  CCCCCTG                             427
```

( 2 ) INFORMATION FOR SEQ ID NO: 11:

( i ) SEQUENCE CHARACTERISTICS:
        ( A ) LENGTH: 286
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 11:

```
CATCATGTAA  TGACGNNGAA  GNAGTGCACA  GATTTGGAAA  CAGATNAACC    50

GCAGTCGCCA  ATCTNTGACC  CTTATTGACT  GTNTGATCTT  AAGCAAGTTG   100

CTTAACCTTT  CAGAATCTTT  NTNCTTTTAA  NTNAAATAGG  AGAATAGAGT   150
```

```
ACCTAACTGA  TAGGTTTNTN  GTNAGGGCTT  ANTGAGAGAA  TGTATGTATG   200

GTAGCCATTT  TCCAAATAAA  GNAGCTATTC  TCCAATAATG  GCTCCCCAGT   250

AAGCTTTACC  TCCTGGTATT  CACACCCAAG  ACCCCT                   286
```

( 2 ) INFORMATION FOR SEQ ID NO: 12:

( i ) SEQUENCE CHARACTERISTICS:
        ( A ) LENGTH: 305
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 12:

```
NNGNNTCTTG  NTACTAATTA  NTAGCAGCAT  GAATGCGTAG  AGAGAGCACA   50

GATTTGGAAA  CAGNTAACCG  CAGTCCCAAT  CTCTNACCCT  TATTNACTGT   100

GTGATCTTAA  GCAAGTTGCT  TAACCTTTCA  GAATCTTTNT  TCTTNTAAAT   150

GAAATAGGAG  AATAGAGTAC  CTAACTGATA  GGNTTGTGNT  GAGGGCTTAA   200

NTAGAGANTN  TATGTATGGT  AGCCATTTTC  CAAATAAAGC  AGCTATTCTC   250

CAATAATGNC  TCCCCAGTAA  GCTTTACCTC  CTGGTATTCA  CACCCAAGNC   300

CCCTT                                                        305
```

( 2 ) INFORMATION FOR SEQ ID NO: 13:

( i ) SEQUENCE CHARACTERISTICS:
        ( A ) LENGTH: 136
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 13:

```
NNGGGTCTTG  TTAGTGAATT  GTGACTTTNA  TCATTTGGAA  ATAGCCTTCT   50

TTTCTNTTAA  TATTTTAGGT  ATCTNTTTTG  TAAACAGCAT  ACACAGTAGT   100

CCCCACTTAG  CAGAGGGGGA  TAGTTCCAAG  ACCCCT                   136
```

( 2 ) INFORMATION FOR SEQ ID NO: 14:

( i ) SEQUENCE CHARACTERISTICS:
        ( A ) LENGTH: 143
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 14:

```
AGGGGTCTTG  GCCTCACATA  CAGCAGGTGT  CTATAAATNT  TTNTTTAATA   50

AATGATTTAT  ACTAGTGCAG  TTTCACTATC  ACAGTTACTT  ACCTTTNTNA   100

GTGTGACAAA  CACAGTCACT  GAAAACCATA  CATCAGGACC  CCT          143
```

( 2 ) INFORMATION FOR SEQ ID NO: 15:

( i ) SEQUENCE CHARACTERISTICS:
        ( A ) LENGTH: 511
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 15:

| AGGGGTCTTG | CAGTGATGGT | TATNCTACTG | ACACCTGGTG | ACAAGAATGG | 50 |
| GAATTCTCTG | ANGTAATCTC | AAGTTAAATG | TTACCTCATT | TTNTTCTATA | 100 |
| GGTAATGGAA | GCATAACATC | ATTGATTAG | CAGATAGGAC | AATATTTCTG | 150 |
| CAATTNTCAT | CATGGTGGCA | CAAGCATCAC | ATTTTTNNTN | GCCATTGGTA | 200 |
| TTTNGATAAA | GTTTTCAAAA | GTTACTGCAA | TTNGTTATCA | GAACACTTGG | 250 |
| GTACTGTGTT | TGCNGATCAG | ACAGANGACT | ATTAANGCCA | AAAGTATTAA | 300 |
| NGAGCTAACA | AGCAAAGCCA | TCCAATACAA | GGCATGTTTT | NACAANTNAT | 350 |
| ATATCTNGTA | GGCAGCTTCA | AAATTAATAG | TTGAAAGTCC | AGAAATCACC | 400 |
| ACAGGNTATC | ATTTGAGGCC | TTAAAACATA | NCTGGAAATN | TTTNTTGAGN | 450 |
| ATTAATNCAA | AANCCTAAGC | NAGGCNATGT | TANNNCCTTA | GCNTTATTTT | 500 |
| NCAGGATGTT | T | | | | 511 |

( 2 ) INFORMATION FOR SEQ ID NO: 16:

( i ) SEQUENCE CHARACTERISTICS:
        ( A ) LENGTH: 370
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 16:

| ACCAGGGNTC | TNGNTCGTGG | CCGGGCTTGT | GGGTCCAGGC | TTGCTACTGN | 50 |
| AANGTTGAAC | TNGAGCGAGG | TAATAGCATA | GGTAAAGCAA | GATGNCTTGA | 100 |
| CAACGGAGGC | ATCATTTNAG | ATGGGANGTA | GTGGGCTGTA | TTGGATGGCA | 150 |
| AAAGCCAGAA | GACTGGGGGT | TGAAGCCTTG | CCCATTGCTG | ACATTTTAAA | 200 |
| TAATACTGGG | NTCTCTATTT | TCCCATCTGA | AAAACAAGAT | CTCCNGTATC | 250 |
| TTAAAAATGT | TCGGCACGTT | GTNTGCCTNC | ATTCATTTAA | TTCATTCTAC | 300 |
| AAAAGGGTTN | ANGCNCCTTC | CANTGTGACC | CNACACTTGG | GATAAGNGNN | 350 |
| TGGGGACATN | AGGTAAAGTA | | | | 370 |

( 2 ) INFORMATION FOR SEQ ID NO: 17:

( i ) SEQUENCE CHARACTERISTICS:
        ( A ) LENGTH: 261
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 17:

| AGGGGTNTTG | AAAGAGGTAA | TGGATGTNAG | ATGAGGCTAC | TAGAGTGAGC | 50 |
| CCTAATCCAG | AGTGACTGGT | GTCCTTTTAT | GAAGGGGAGA | TTATAACAAA | 100 |
| GACACAGACA | GAGGGATGAC | TGTNAGAGGA | CACAGAGAAC | AGGTGGCCGT | 150 |
| CTACAAGGCA | AGGAGAGAGG | CCTTGGGAGA | AACCAACCCT | GCAGACACTG | 200 |
| TGCTCTGGGA | CTTCCAGCCT | NCAGATATGT | GAGAAAATAC | ATTTNTTGTT | 250 |
| CCAAGACCCC | T | | | | 261 |

( 2 ) INFORMATION FOR SEQ ID NO: 18:

( i ) SEQUENCE CHARACTERISTICS:
        ( A ) LENGTH: 169
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 18:

```
AGGGGNCTTG  GNAGCCATAT  TCTNCATTTC  CNTGGANAGA  TGCATGTNGA   50
CCTTAGCCTG  CTAAAAGCAC  TTGTTTNCGG  NGNTCCNTNA  CTNAGTNCAG  100
NGNCCGGTNG  NGCGNTTCCT  GGNCCCCTTT  GNAAGACCCN  TGGGCTAGAG  150
CGGACGAAAT  NGTGTNTNA                                       169
```

( 2 ) INFORMATION FOR SEQ ID NO: 19:

( i ) SEQUENCE CHARACTERISTICS:
        ( A ) LENGTH: 386
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 19:

```
AGGGGTCTTG  AGGTGATTGA  CTTGCAAATA  ATCTTGTGCT  CTTAAAGCAC   50
ATTTTTGGTA  AATTTTCAAA  TTTCTGAATA  CTAGAAATNA  TTTCTTTAGT  100
TATAATTGAG  TGAGATCAGA  TATTCACAGA  CTAATAGACT  CTCAAAACCA  150
GTGGGTGCNG  CCTTCATACC  ACACATTTNA  CCATGCTAGG  NTAAACATTC  200
ATCTTCAATT  TTNTNGTTGT  TAAAAAACAT  ACTTCACCAA  GGNATTTATT  250
ATCCCACTCA  TTTTATCACA  TACCTCTNCT  GGNGCTTAGG  GTCTCAGGCC  300
CTTCCTGTCG  TCTNCTTTGG  TGNCTCCCCT  GCTAAANCCC  TACCACACTT  350
TGGNGTTTTT  NAGGGTTTCT  NAACCTTAAG  TAAAGT                  386
```

( 2 ) INFORMATION FOR SEQ ID NO: 20:

( i ) SEQUENCE CHARACTERISTICS:
        ( A ) LENGTH: 395
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 20:

```
AGGGGTCTTG  AGGTGATTGA  NTTGCAAATA  ATCTTGTGCT  CTTAAAGCAC   50
ATTTTTGGTA  AATTTTCAAA  TTTCTGAATA  CTAGAAATTA  TTTCTTTAGT  100
TATAATTGAG  TGAGATCAGA  TATTCACAGA  CTAATAGACT  CTCAAAACCA  150
GTGGGTGCTG  CCTTCATACC  ACACATTTTA  CCATGCTAGG  NTAAACATTC  200
ATCTTCAATN  TTTTNGTTGT  TAAAAAACAT  ACTTCACCAA  GGAATTTATT  250
ATCCCACTCA  TTTTATCACA  TACCTCTTCT  GGAGCTTAGG  GTCTCAGNCC  300
CTTCCTGTCT  CTNCTTTGGT  GTCTCCCCTG  CTACANCCNT  ACCACACTTT  350
GGNGTTTTTG  NGGGTTCTTA  ATCTTAAGTA  AAGTGTGAAT  AAAAA       395
```

( 2 ) INFORMATION FOR SEQ ID NO: 21:

( i ) SEQUENCE CHARACTERISTICS:
        ( A ) LENGTH: 136
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 21:

```
AGGGGTCTTG  GAACTATCCC  CCTCTGCTAA  GTGGGGACTA  CTGTGTATGC   50
TGTTTACAAA  ACAGATACCT  AAAATATTAA  CAGAAAAGAA  GGNTATTTCC  100
AAATGATAAA  AGTCACAATT  CACTAACAAG  ACCCCT                  136
```

( 2 ) INFORMATION FOR SEQ ID NO: 22:

( i ) SEQUENCE CHARACTERISTICS:
        ( A ) LENGTH: 237
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 22:

```
AGGGGNCTTG  GAACAAAAAA  GACTATAAGA  TCAGAGGTAA  TGAGGTTGGG   50
ATAGAGATAT  GTGGATGAAC  CTATGAACAC  AAAATATAAA  GATCTCATGT  100
TTAATGCTCA  TATTAATACT  CACCAGAAAG  CGTAGAATAA  CATTGGCTGA  150
GTATGGTGGC  TCTTTGAAAG  GCTGAGGTGG  GAGGNTCACT  TGATGCCAGT  200
AGTTTAAGAC  CAGCTTGGGC  AACATAGCAA  GACCCCT                 237
```

( 2 ) INFORMATION FOR SEQ ID NO: 23:

( i ) SEQUENCE CHARACTERISTICS:
        ( A ) LENGTH: 383
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 23:

```
AACTGNNGCT  GCANAATTAA  GTCCAAAACA  GNAAAAGGAA  CAAAATATTA   50
AGCTAATTCC  ACTCATACAA  AATGTCTAGT  AAATTCCCAG  AGGNGAATGG  100
GCAAATTCAT  AGAGACAGAA  AACAGATTAG  AAGTTATCAA  AGACAGGACA  150
AGAGGAGAAC  AGAGTTACTG  CTTAATGGTT  ACAGAATTTT  TGTTTGGGGT  200
GATAAAAAGT  TATAAAANTA  CTGGTGATGG  TTGCATAACA  TTGTGAATAC  250
AACTAATGCC  ACTGAATTGC  ACATTTAAAA  TGTTAAATGG  CAAATTTTAT  300
GTTATGTATA  TTTTCCACAG  CTTAAAAAGT  AATAATGTAA  TATNCCAAAA  350
CCCATTGAAT  TGTNCACTTT  AAATGGGTAA  TTT                     383
```

( 2 ) INFORMATION FOR SEQ ID NO: 24:

( i ) SEQUENCE CHARACTERISTICS:
        ( A ) LENGTH: 305
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 24:

```
AGGGGNCTTG  GGTGTGAATA  CCAGGAGGTA  AAGCTTACTG  GGGAGCCATT   50
ATTGGAGAAT  AGCTGCTTTA  TTTGGAAAAT  GGCTACCATA  CATACATTCT  100
CTCATTAAGC  CCTCACAACA  ATCCTATCAG  TTAGGTACTC  TATTCTCCTA  150
TTTCATTTAA  AAGAACAAAG  ATTCTGAAAG  GTTAAGCAAC  TTGCTTAAGA  200
TCACACAGTC  AATAAGGGTC  AGAGATTGGG  ACCTGCGGTT  ATCTGTTTCC  250
AAATCTGTGC  TCTCTCTACG  NATTCATGCT  GCTATTAATT  AGTATCAAGA  300
CCCCT                                                      305
```

( 2 ) INFORMATION FOR SEQ ID NO: 25:

( i ) SEQUENCE CHARACTERISTICS:
    ( A ) LENGTH: 306
    ( B ) TYPE: NUCLEIC ACID
    ( C ) STRANDEDNESS: SINGLE
    ( D ) TOPOLOGY: LINEAR ( i v ) ANTI-SENSE: NO ( x i ) SEQUENCE DESCRIPTION: SEQ ID NO: 25:

```
AGGGGTCTTG  GGTGTGAATA  CCAGGAGGTA  AAGCTTACTG  GGGAGCCATT   50
ATTGGAGAAT  AGCTGCTTTA  TTTGGAAAAT  GGCTACCATA  CATACATTCT  100
CTCATTAAGC  CCTCACAACA  ATCCTATCAG  TTAGGTACTC  TATNCTCCTA  150
TTTCATTTAA  AAGANCAAAG  ATTCTGAAAG  GTTAAGCAAC  TTGCTTAAGA  200
TCACACAGTC  AATAAGGGTC  AGAGATTGGG  ACCTGCGGTT  ATCTGTTTCC  250
AAATCTGTGC  TCTCTCTACG  CATTCATGCT  GCTATTAATT  AGTATCAAGA  300
CCCCTG                                                     306
```

( 2 ) INFORMATION FOR SEQ ID NO: 26:

( i ) SEQUENCE CHARACTERISTICS:
    ( A ) LENGTH: 446
    ( B ) TYPE: NUCLEIC ACID
    ( C ) STRANDEDNESS: SINGLE
    ( D ) TOPOLOGY: LINEAR ( i v ) ANTI-SENSE: NO ( x i ) SEQUENCE DESCRIPTION: SEQ ID NO: 26:

```
ANGGGGGNAC  TTNACTGTAT  GGGTTTNNAG  NGACCTNTTT  TTTNNNACAC   50
TCAGAAANGG  TAAGNAANTG  TNATAGNNAA  ACTNCNCTAG  GATAATCNAT  100
TTTNTTAAAC  AAACATTTNT  NGACNCCNNN  NTGTTNTNTN  AGGCCAAGAC  150
CCNCTGGGGT  NAGANGTGGG  CCCCNACCCG  GGGGNGGGGG  GCNCCCACCT  200
TTTTTTTNNC  CCCNTTTAAN  NGNGGGGGGG  TTNAATTGCC  CCNGTTTTTG  250
GGGGTNAANN  NAATNGGGNC  CANAAGGANT  GTTTTTTCCC  NCNGGGGGGA  300
AAAANATTGT  TTTTACCCNC  GNTTNCNAAA  AAATTTCCCT  ANNTNATATA  350
TNNNTTGNGG  GGTGCCNCNN  GAAGNGNNTA  TTAAAGAGTT  GTTANANNAC  400
CNCTTNGNGG  GGGCGCCCNN  AATTGGGGGG  GGNGGTCNTA  CACCTN      446
```

( 2 ) INFORMATION FOR SEQ ID NO: 27:

( i ) SEQUENCE CHARACTERISTICS:

```
    ( A ) LENGTH: 396
    ( B ) TYPE: NUCLEIC ACID
    ( C ) STRANDEDNESS: SINGLE
    ( D ) TOPOLOGY: LINEAR ( i v ) ANTI-SENSE: NO ( x i ) SEQUENCE DESCRIPTION: SEQ ID NO: 27:

AGGGGTCTTG GGCCCAGACA GACATGGGTT CAATTTATAG CACTGATAAT    50
GTATAGCTGT GGGNCCTCGT GCAGTGATTT AACCTCTGAA AGTTTTCTCA   100
CCTTTAAATG GTGAGGAAAA TACTGATGTG AAAAATATAC AAAAGNAAAC   150
ACGCAAAGCA CCTAGCCTTG CTGGAAACAT CAGTTACTCA TGATGNTGAT   200
CATGATGATG CCAATGATAA TNNTGATAAT GGNGTTAATN NTGGTGATGA   250
AGACTGATCA CAGNCTGCCC TTCTTTTTTG NGGAATTTGG GAAAATGAAA   300
TCTCTTTGAT TCCCACTAAT GCNTTAAGC TGTGTCANGC AACNGATGGG    350
TTGGGGAGGT GGATNGGGGT GACTCAATAT TTAGGTNCCT GCNCTT       396

( 2 ) INFORMATION FOR SEQ ID NO: 28:

( i ) SEQUENCE CHARACTERISTICS:
        ( A ) LENGTH: 136
        ( B ) TYPE: NUCLEIC ACID
        ( C ) STRANDEDNESS: SINGLE
        ( D ) TOPOLOGY: LINEAR ( i v ) ANTI-SENSE: NO ( x i ) SEQUENCE DESCRIPTION: SEQ ID NO: 28:

AGGGGTCTTG GAACTATCCC CCTCTGCTAA GTGGGGACTA CTGTGTATGC    50
TGTTTACAAA ACAGATACCT AAAATATTAA CAGAAAAGAA GGNTATTTCC   100
AAATGATAAA AGTCACAATT CACTAACAAG ACCCCT                  136
```

METHODS FOR PROFILING MRNA EXPRESSION IN NEURITES

INTRODUCTION

This invention was made in the course of research sponsored by the National Institutes of Health. The U.S. Government may have certain rights in this invention.

BACKGROUND OF THE INVENTION

In recent years there has been great progress in the understanding of the genetic basis of neuropsychiatric disorders including those associated with mental retardation. While the genetic defects of such disorders are disparate and each mechanism appears to be novel, the unifying theme behind the development of these diseases is brain development and maintenance of neurological networks.

Neurological networks are made up of individual neurons, each neuron being a separate structural and functional cellular unit. Neurons have special features for the reception of nerve impulses from other neurons, the effect of which may be either excitation or inhibition, and conduction of nerve impulses. Neurons commonly have long cytoplasmic processes known as neurites which end in close apposition to the surfaces of other cells. The ends of these neurites are called synaptic terminals and the cell-to-cell contacts they make are known as synapses. The neurites in higher animals are usually specialized to form dendrites and axons which conduct impulses toward and away from the cell body, respectively. The arrival of an impulse at a terminal triggers the process of synaptic transmission. This event usually involves the release of a chemical compound from the neuronal cytoplasm invoking a response in the postsynaptic cell. Neurons of the central nervous system consist of discrete segments including the cell body, the dendrites and the axon. While most nerve cells conform to this basic structure, there is a wide range of structural diversity based upon the specific function of the cell within the body.

It has been shown that these polarized cells contain a variety of cytoplasmic and membrane-bound proteins differentially distributed throughout the axon, dendrites, and cell body of the neuron. It is believed that neurons of the central nervous system synthesize proteins locally, at or near postsynaptic sites which are independent of the cell body. Ultrastructural studies have revealed that polyribosomes are preferentially located either beneath post-synaptic sites or occasionally associated with membrane specializations on dendrites. It has been suggested that these anatomical structures represent the protein synthetic machinery necessary to translate and post-translationally modify different classes of protein in neurons. An energy-dependent mechanism for the selective transport of RNA in neurons has also been shown. The nature and distribution of the RNAs present in these cells, however, is poorly understood.

In situ hybridization (ISH) studies have been successful in identifying very few mRNAs in neuronal processes. Studies using in situ hybridization and Northern blot analyses of synaptosomal RNA fractions with the AMPA-GluR1, -GluR2, GluR3 and GluR-4 and kainate-sensitive GluR5 and GluR6 receptor subunits failed to reveal mRNAs at dendritic locations. (Craig, A. et al., *Neuron* 1993, 10, 1055–1068; Chicurel, M. et al. *J. Neurosci* 1993, 13, 4054–4063).

Microdissection of individual neurites has now revealed a large number of mRNAs, including members of the glutamate receptor family, second messenger components, and components of the translational control apparatus, present in hippocampal neurites. It has now been found that the profiles of expressed mRNAs from discrete segments of the same neurons have different characteristics. These differences in expressed mRNA can be used as a means to specifically target discrete segments of the neuron and to identify and diagnose genetic neurological disorders at the molecular level.

SUMMARY OF THE INVENTION

An object of the invention is to provide a method of identifying neurite cDNA clones which comprises determining the mRNA expression in selected neurites, comparing the relative levels of mRNA expression, and identifying neurite cDNA clones based on the level of mRNA expression.

Another object of the invention is to provide neurite cDNA clones.

Another object of the present invention is to provide a method of profiling mRNA expression in a selected neurite which comprises converting an mRNA population in a soma or process of a selected neurite into cDNA, making the cDNA double stranded, linearly amplifying the double stranded cDNA into aRNA, and using the aRNA as a probe in reverse phase Northern analysis to produce an mRNA expression profile.

Another object of the present invention is to provide a method of diagnosing a condition associated with an mRNA expression pattern which comprises determining the relative levels of mRNA expression in selected cells associated with a selected condition, comparing the relative levels determined with established controls, and diagnosing a condition based upon the comparison of the mRNA expression levels.

Yet another object of the present invention is to provide a method of treating a condition associated with an mRNA expression pattern which comprises determining the relative levels of mRNA expression in selected cells associated with a selected condition, and altering the relative levels with an effective amount of an agent capable of altering mRNA expression.

BRIEF DESCRIPTION OF THE FIGURES

In FIGS. 1B and 1D, the corresponding soma (HP 3-9 in FIG. 1B, and HP2-13 in FIG. 1D) were isolated. In addition to the large number of mRNAs expressed in some neurites (for example, lane 5 in FIG. 1B), there are some commonly shared PCR products between neurites or neurite segments (closed arrowheads) and between neurites and their cell bodies (open arrowheads). These data were reproduced a minimum of three times. In FIGS. 1A, 1C, and 1E, a phase-contrast photomicrograph of the cell and the neurites of interest prior to isolation are shown. Dark bars perpendicular to each process represent the approximate transection point.

DETAILED DESCRIPTION OF THE INVENTION

Figure 1A:
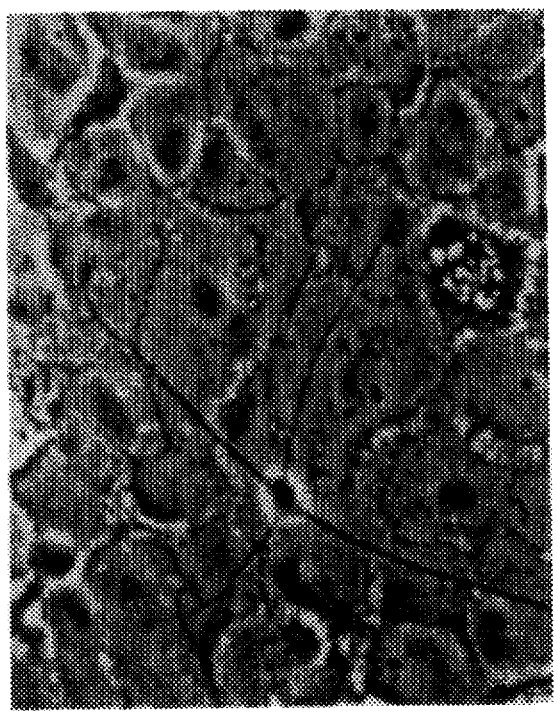
FIGS. 1A–1F are a differential display of three representative cells. A single oligonucleotide, OPA-5, served as the 3'-primer. In combination with three different modified oligo-dT$_{11}$ primers (oligo A, 5'-T$_{11}$AC-3'; oligo B, 5'-T$_{11}$CA-3'; oligo C, 5'-T$_{11}$GC-3'), differential display reactions were carried out on separate neurites (HP3-7 and HP3-8) (FIG. 1B), proximal (HP2-10) and distal (HP2-12) segments of the same process as well as another separate process (HP2-11) (FIG. 1D), and distal branch points (HP3-5 and HP3-6) of the same process (FIG. 1F) from single hippocampal cells. Each of these neurites were isolated as described in Example 1.

Different regions of the central nervous system are populated by functionally and anatomically distinct synaptic connections. During synapse construction, maintenance and remodeling, it is believed that proteins are selectively transported to these distinct connections. As a result, the specificity of the nervous system is established and modified, at least in part, by these protein targeting mechanisms. It has now been found that mRNA expression profiles are specific for messages seen in neurites. A method has now been developed for identifying neurite cDNA clones by determining the mRNA expression in selected neurites, comparing the relative levels of mRNA expression, and identifying neurite cDNA clones based on the level of mRNA expression.

Isolated hippocampal cells free of overlapping processes from neighboring cells were identified in low density cultures. Under these conditions, neurons grow as isolated cells or in small 2–4 cell groups, either directly on the substrate or on glial cells. Neurons are identified by morphological criteria involving synaptic interactions. Individual proximal and distal neurites were harvested by transecting them at varying distances from the cell body and aspirating them into a micropipette containing the reagents necessary for the first step in the antisense RNA (aRNA) amplification procedure. In a number of cases, multiple processes were isolated from a single cell followed by the aspiration of the cell body. Individual neurites or cell bodies were processed through the following aRNA amplification procedure to produce an mRNA expression profile. The mRNA population in the cell soma or cell process was converted into a complementary DNA (cDNA) using an oligo-dT-T7 primer. After the cDNA was made double-stranded, it was linearly amplified into aRNA using T7 RNA polymerase. For reverse Northern analysis, aRNAs served as a probe for mRNA expression profiles. In subsequent experiments, aRNAs were made into double-stranded cDNAs and used as templates for experiments using the polymerase chain reaction (PCR).

The population of the mRNAs in neurites was assessed initially by mRNA expression profiling. Southern blots containing cloned cDNAs encoding members of the ionotropic glutamate receptor family were probed with radiolabeled aRNA from individual neurites or cell bodies. Glutamate receptors, classified into N-methyl-D-aspartate (NMDA), α-amino-3-hydroxy-5-methyl-isoxazole-4-propionate (AMPA; GluR1-4), and kainate (GluR5-7) subtypes are the primary mediators of excitatory synaptic transmission in the brain. These receptors also play a role in the biochemical events associated with excitotoxicity and long-term potentiation (LTP), a specialized form of synaptic plasticity. The qualitative mRNA expression of multiple members of the glutamate receptor family was examined. All neurites expressed GluR1, GluR2, GluR4 and NMDAR1 mRNA. In a majority of neurites, mRNA expression of GluR3 (15/19), GluR5 (14/19), was observed; while expression for GluR6 mRNA was detectable in approximately one half the neurites studied. The presence of these subunits was confirmed by subunit specific PCR. In contrast, only one neurite showed detectable hybridization signals for NR2a and NR2c mRNA. Thus, neurite cDNA clones may be identified by determining the mRNA expression for glutamate receptors. Examples of preferred glutamate receptors include, but are not limited to, GluR1, GluR2, GluR3, GluR4, GluR5, GluR6, GluR7, NR2a and NR2b.

A number of neurite cDNA clones have now been identified in accordance with the methods of the present invention. Two of these clones have been found to correspond to farnesyl diphosphate (FPP) synthase mRNA identified in two separate distal processes. As part of the isoprene biosynthetic pathway, FPP synthase generates the farnesyl moiety ultimately transferred to the COOH-terminal CaaX motif of mammalian ras proteins. Two other cDNAs have been found to have sequence similarity with mRNAs for the γ-subunit of the interleukin-2 receptor and the tumor necrosis factor inducible protein A20. The remaining cDNA clones have little sequence similarity with any published gene sequences. By sequencing the cDNA clones corresponding to full-length RNAs, it is possible to identify the role the primary sequence and secondary structural characteristics of the mRNA play as recognition elements in targeting and transport of the mRNA. The cDNA clones of the present invention are identified in Table 1 as SEQ ID NO: 1 through SEQ ID NO: 28.

TABLE 1

| CLONE | SEQ ID NO: |
|---|---|
| 57-3 | SEQ ID NO: 1 |
| 59-3 | SEQ ID NO: 2 |
| 60-3 | SEQ ID NO: 3 |
| 63-3 | SEQ ID NO: 4 |
| 64-3 | SEQ ID NO: 5 |
| 65-3 | SEQ ID NO: 6 |
| 66-3 | SEQ ID NO: 7 |
| 67-3 | SEQ ID NO: 8 |
| 68-3 | SEQ ID NO: 9 |
| 70-3 | SEQ ID NO: 10 |
| 71-3 | SEQ ID NO: 11 |
| 72-3 | SEQ ID NO: 12 |
| 73-3 | SEQ ID NO: 13 |
| 76-3 | SEQ ID NO: 14 |
| 78-3 | SEQ ID NO: 15 |
| 60-7 | SEQ ID NO: 16 |
| 63-7 | SEQ ID NO: 17 |
| 64-7 | SEQ ID NO: 18 |
| 66-7 | SEQ ID NO: 19 |
| 67-7 | SEQ ID NO: 20 |
| 68-7 | SEQ ID NO: 21 |
| 69-7 | SEQ ID NO: 22 |
| 70-7 | SEQ ID NO: 23 |
| 71-7 | SEQ ID NO: 24 |
| 72-7 | SEQ ID NO: 25 |
| 74-7 | SEQ ID NO: 26 |
| 78-7 | SEQ ID NO: 27 |
| 100-7 | SEQ ID NO: 28 |

The cDNA clones of the present invention can be used in the diagnosis of neuropsychiatric diseases. Human genes containing unstable triplet repeats are associated with several neuropsychiatric diseases including, but not limited to, Huntington's disease, spinal and bulbar muscular atrophy and spinocerebellar ataxia type 1. These diseases show a variety of clinical symptoms making them difficult to diagnose. However, an understanding of these diseases at the molecular level provides the diagnostic laboratory with the capability to test directly whether an individual's DNA contains the disease-causing mutation, either as a confirmation of a clinical diagnosis or prior to any symptoms. For example, fragile X chromosomes, associated with mental retardation in most males that have it and, to a lesser degree, some of the females heterozygous for it, can be identified using cDNA clones of the present invention having SEQ ID NO: 1 through 15. The cDNA clones of the present invention can also be used in prenatal screening.

Distinct relative variations in mRNA expression have also been identified using reverse Northern blot analysis. Differences in the relative levels of glutamate receptor mRNAs expressed between a neuronal process or processes from the same cell and its cell body have been observed. In a number of cells, the qualitative expression patterns were very similar, yet the relative intensity of the hybridization signal was more profound for specific subunits. For example, relative levels of NMDAR1 and GluR5 mRNA were clearly elevated in HP9a, the apical neurite, versus HP9b, the basal neurite, or the soma. This tendency was complimented in other cells which displayed a more differentiated qualitative pattern of glutamate receptor mRNA expression. This differentiated pattern of mRNA expression contributes to the physiological function of a synapse. These differences in the relative levels of mRNA expression result in the occurrence of different neuronal processes in the same cell. In addition to glutamate receptors, the expression of several other cDNAs has been assessed with reverse Northern blot analysis. Previous reports have demonstrated the dendritic localization of the α-subunits of the $Ca_{2+}$/calmodulin-dependent protein kinase (CaMK II) mRNA. It has now been found that mRNA expression in distal and proximal segments of isolated neurites is strongly positive for CaMK II. Thus, specific segments and processes of a neuron may be targeted by determining the profile of mRNA expression involved in the process, identifying an mRNA with a high level of expression and targeting an agent to that mRNA.

Alzheimer's disease, amyotrophic lateral sclerosis, Huntington's disease and epilepsy are all examples of disorders which involve the degeneration of specific groups of neurons in discrete regions of the nervous system. It appears that different regions of the nervous systems, and specifically, different types of neurons possess different sensitivities to agents. Therefore, to assess the neurotoxicity of an agent, the agent should be assessed in neurons isolated from different regions since it appears that some neuron types are more sensitive than others. It has now been found, however, that neuron types can be identified by determining the mRNA expression in selected neurons, comparing levels of mRNA expression in the selected neurons with levels in known neurons, and identifying the neuron type based on the level of mRNA expression. Thus, the neurotoxicity of an agent for a specific neuron type may be assessed in a culture of mixed neuron types. In this method, it is preferred that mRNA expression is determined by an aRNA amplification procedure.

Figure 1B:
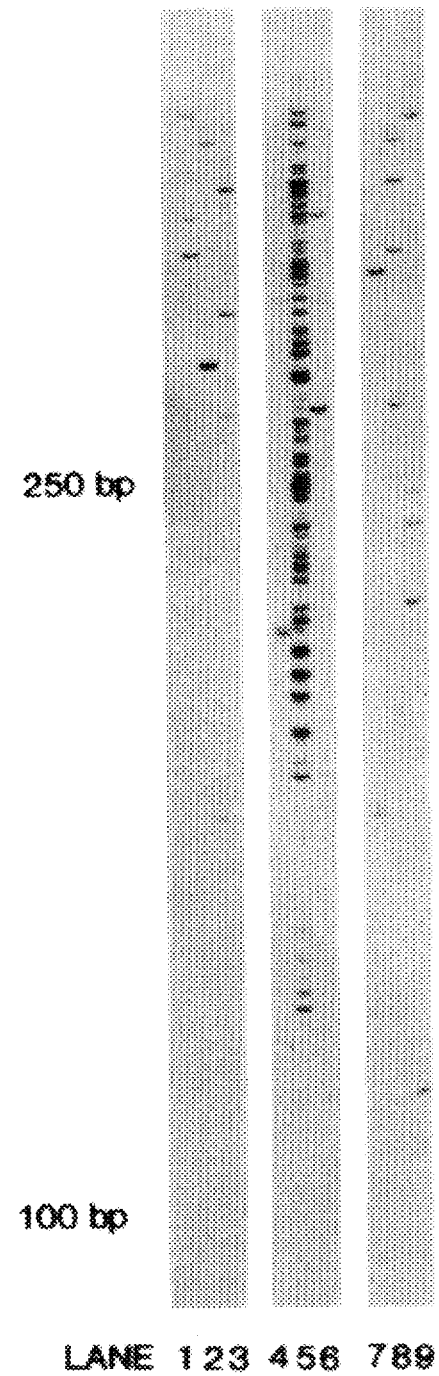
Figure 1C:
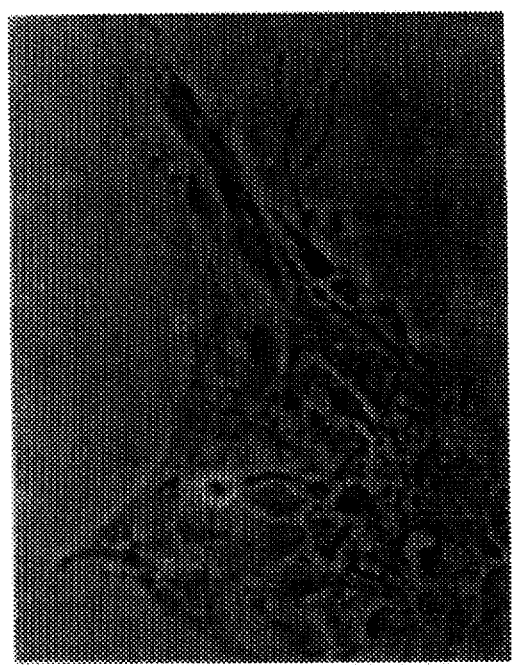
Figure 1D:
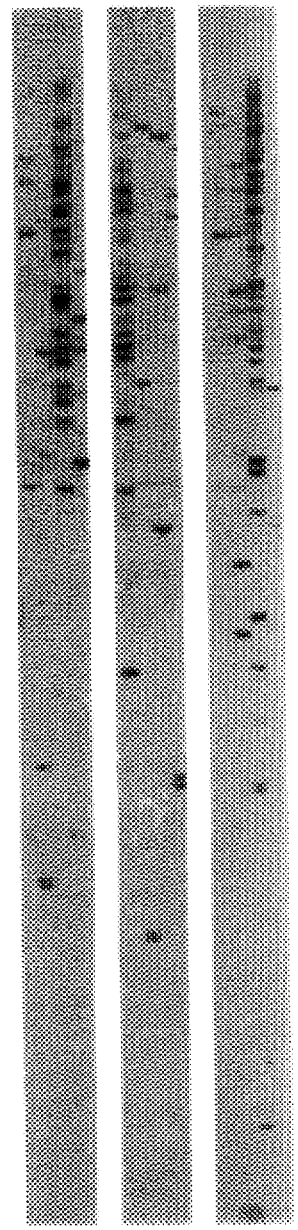
Figure 1E:
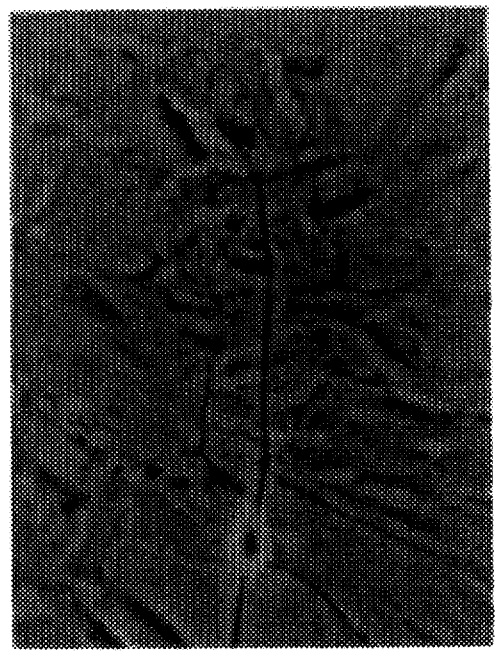
Figure 1F:
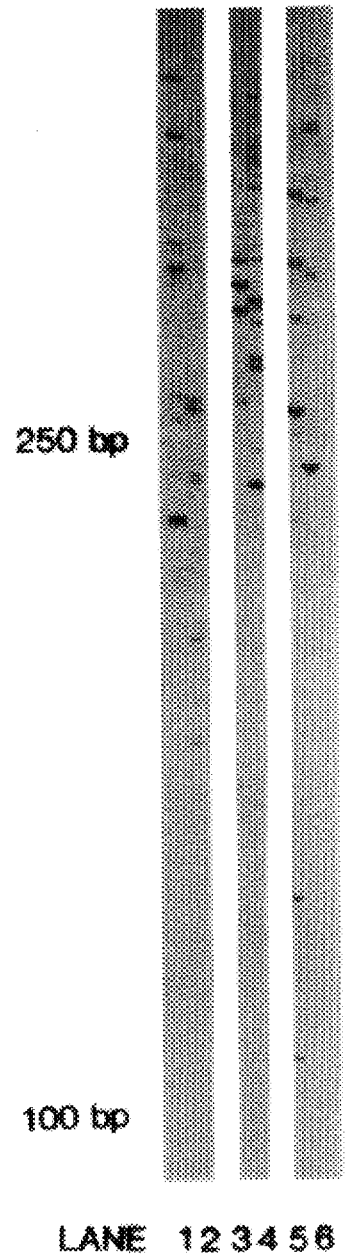

The complexity of mRNA expression in neurons was investigated further using a PCR-based assay, differential display developed by Liang P. et al., Science 1993, 257, 967-970. In these experiments, a single 10 mer (OPA-5;5'-AGGGGTCTTG-3', SEQ ID NO: 29) which serves as the 5'-primer and a modified polythymidine primer containing a two base extension were used to amplify specific populations of the polyadenylated RNA pool. In each of these reactions, banding patterns unique to the soma or process and the combination of primers used were observed. Differential display (DD) of mRNAs from three sets of cells are shown in FIG. 1. The complement of DD profile of neurites exhibited a large number of mRNA species. These patterns of PCR products indicate that mRNAs are differentially distributed. For example, in a typical cell in which two neurites are transected and isolated, there are transcripts that migrate at similar molecular sizes between individual neurites. This circumstance is repeatedly seen in proximal and distal segments of the same process and in distal branch points of a single process. While there are some products found concomitantly in one or more neurites and between neurites and their corresponding cell bodies, there are numerous transcripts that are unique to individual neurites or segments of individual neurites. Samples of media and tRNA did not display any banding pattern using differential display.

The contamination of neurites with surrounding glia or astroglial processes was assessed by glial fibrillary acidic protein (GFAP) mRNA. Neurite and soma preparations used in these experiments were determined to be free of GFAP mRNA. The existence of multiple mRNAs in neuronal processes suggests that mRNA transport and local protein synthesis plays a role in the regulation of neuronal physiology, development and regeneration.

In the present invention, mRNA expression patterns can be used to diagnose conditions related to the presence or absence of synthesized proteins. In recent years, several human neurological diseases have been identified resulting from the expansion of trinucleotide repeats. These triplet repeats are normally polymorphic and exonic, though not always coding. In disease states, they become markedly unstable and may expand moderately or by thousands of repeats in a single generation thereby altering gene expression, message stability or protein structure. Thus, in a diseased state, alterations in normal mRNA expression patterns or profiles would be expected. Methods related to diagnosing a condition associated with an mRNA expression pattern comprise determining the relative levels of mRNA expression in selected cells associated with a selected condition; comparing the relative levels determined with established controls; and diagnosing a condition based upon the comparison of the mRNA expression levels. In this method, it is preferred that the selected cells are neurons.

Measuring of mRNA expression patterns as disclosed in the present invention can also be used in methods for treating a condition associated with an mRNA expression pattern. Levels of mRNA expression in selected cells associated with a selected condition are determined and compared to normal levels in the same type of cells. If the level of mRNA expression is abnormal, an effective amount of an agent capable of altering mRNA expression is administered. In this method, it is preferred that the mRNA expression levels be measured in neurons. Examples of agents capable of altering mRNA expression include, but are not limited to, antisense oligonucleotides and pharmacological agents such as dopamine, serotonin and cyclic AMP. Such agents are administered in an effective amount either alone or in conjunction with a suitable pharmaceutically acceptable carrier. By "effective amount" it is meant a concentration of an agent to be administered which is sufficient to modulate expression of mRNA. Such concentrations can be routinely determined by those of skill in the art upon this disclosure and will depend upon the age, weight and condition of a patient. Suitable pharmaceutically acceptable carriers are well known in the art and are described for example in Gennaro, Alfonso, Ed., *Remington's Pharmaceutical Sciences*, 18th Edition 1990. Mack Publishing Co., Easton, Pa., a standard reference text in this field. Pharmaceutical carriers may be selected in accordance with the intended route of administration and the standard pharmaceutical practice.

The following nonlimiting examples are provided for illustrative purposes.

EXAMPLES

Example 1

Preparation of Neurites

Hippocampi were dissected from ED20-21 rat fetuses, dissociated in trypsin and plated at 30,000–100,000 viable cells/ml of media onto poly-lysine covered glass coverslips held in 35 mm tissue culture petri dishes. One day after plating, 0.5 ml of media was replaced with media containing 20 mM potassium. The cultures were subsequently fed once a week with a drop of the high K⁺ media. Experiments were performed after 21–28 days in culture. Cell bodies and their neurites were taken from cells cultured from different animals on three different days under similar conditions. During each of these sessions, a sample of culture media was also aspirated and processed through aRNA processing to assess the possible presence of mRNAs in the culture media from dying cells.

Example 2

Determination of mRNA Band Patterns

Reactions were carried out in 25 µl volumes using the Hot Start technique (Perkin Elmer, product #N808-0100) with an upper-lower ratio of 1.5 to 1. Reactions contained 200 µM of dATP, dGTP and TTP, 4 µM dCTP, 5 µCi of $^{33}$P-dCTP or 4 µCi $^{32}$P-dCTP or 18.75 µCi of $^{35}$S-dATP (NEN/Dupont), 0.4 µM of OPA-5 or other 10 mers (Operon Technologies), 0.6 µM of oligo A, B or C, 2.5 mM MgCl$_2$, 1.25 units of AmpliTaq polymerase (Perkin Elmer), and 1 µl of a 1:10 dilution of DNA previously processed through a single round of aRNA amplification. Under these conditions, the primers are in vast excess to the amount of template used for the reaction. Reactions were cycled 35 rounds at 94° C. for 30 seconds, 40° C. for 90 seconds and 72° C. for 45 seconds, followed with a final 5 minute elongation at 72° C. in a Biosycler thermocycler. Approximately 5 µl of the reaction was loaded onto a 6% acrylamide/7M urea gel. Gels were vacuum dried and apposed to XAR film. Gels shown in FIG. 1 used $^{33}$P-dCTP. The reactions exhibited a banding pattern unique to a sample.

Example 3 cDNA Synthesis

Micropipettes containing reagents for first strand cDNA synthesis also contained 5 µM dithiothreitol and RNAsin (Promega, Madison, Wis.) at 0.5 units/µl. The efficiency of amplification, as based upon trichloroacetic acid precipitated counts and Northern blot analysis to assess the size distribution of mRNAs, did not differ with or without digitonin. Antisense RNA processed through two rounds of amplification was added to Southern blots containing equal amounts (500 ng) of glutamate receptor cDNAs linearized with the appropriate restriction enzyme and applied by vacuum onto a slot blot apparatus. A random-primed vector cDNA clone, pBluescript SK (Stratagene, La Jolla, Calif.) was added to stripped blots to demonstrate the presence of DNA in each slot. Scanning densitometry analysis was performed on autoradiographs using a Scanning Laser Densitometer (Molecular Dynamics, Sunnyvale, Calif.). Hybridization signals were normalized to ribosomal RNA for each neurite or soma studied.

---

What is claimed:

1. A method of identifying neurite cDNAs comprising:

(a) converting an mRNA population in selected neurites into cDNA;

(b) determining mRNA expression in the selected neurites;

(c) comparing the relative levels of mRNA expression; and (d) identifying neurite cDNAs based on the level of mRNA expression.

2. The method of claim 1 wherein the mRNA expression is determined by an aRNA amplification procedure.

3. A method of profiling mRNA expression in a selected neurite comprising:

(a) converting an mRNA population in a selected neurite into cDNA;

(b) making the cDNA double stranded;

(c) linearly amplifying the double stranded cDNA into aRNA; and (d) using the aRNA as a probe in reverse phase Northern analysis to produce an mRNA expression profile of the selected neurite.

4. The method of claim 3 wherein the mRNA population in the selected neurite is converted into cDNA using an oligo-dT-T7 primer.

5. The method of claim 3 wherein the double stranded cDNA is linearly amplified into aRNA using T7 RNA polymerase.

* * * * *